US011650139B2

(12) United States Patent
Nakao

(10) Patent No.: US 11,650,139 B2
(45) Date of Patent: May 16, 2023

(54) DETECTION METHOD FOR DETECTION DEVICE, CONTROL SYSTEM, DETECTION SYSTEM, AND PROGRAM

(71) Applicant: PANASONIC CORPORATION, Osaka (JP)

(72) Inventor: Atsuo Nakao, Nara (JP)

(73) Assignee: PANASONIC HOLDINGS CORPORATION, Osaka (JP)

( * ) Notice: Subject to any disclaimer, the term of this patent is extended or adjusted under 35 U.S.C. 154(b) by 298 days.

(21) Appl. No.: 17/265,665

(22) PCT Filed: Aug. 6, 2019

(86) PCT No.: PCT/JP2019/030916
§ 371 (c)(1),
(2) Date: Feb. 3, 2021

(87) PCT Pub. No.: WO2020/032029
PCT Pub. Date: Feb. 13, 2020

(65) Prior Publication Data
US 2021/0318209 A1     Oct. 14, 2021

(30) Foreign Application Priority Data

Aug. 8, 2018  (JP) .............................. JP2018-149789

(51) Int. Cl.
*G01N 1/22*       (2006.01)
*G01N 1/40*       (2006.01)

(52) U.S. Cl.
CPC ......... *G01N 1/2247* (2013.01); *G01N 1/2214* (2013.01); *G01N 1/405* (2013.01)

(58) Field of Classification Search
CPC ............... G01N 33/497; G01N 27/227; G01N 1/2247; G01N 1/2214; G01N 1/405
See application file for complete search history.

(56) References Cited

U.S. PATENT DOCUMENTS 6,112,602 A * 9/2000 Mitra .................. G01N 33/1846
                                                                73/863.12
6,244,117 B1 * 6/2001 Mengel ................ G01N 1/2273
                                                                73/863.23
(Continued)

FOREIGN PATENT DOCUMENTS

JP      H10-19862 A     1/1998
JP      2570102 Y2      5/1998
(Continued)

OTHER PUBLICATIONS

International Search Report and Written Opinion issued in International Patent Application No. PCT/JP2019/030916, dated Nov. 5, 2019; with partial English translation.

*Primary Examiner* — David A. Rogers
(74) *Attorney, Agent, or Firm* — McDermott Will & Emery LLP

(57) ABSTRACT

A detection method includes calibration mode of calibrating sensor with low-concentration gas being caused to flow along direction from the sensor toward an adsorption part, first detection mode of, after the calibration mode, detecting chemical substance with sample gas being caused to flow along the direction from the sensor toward the adsorption part, first adsorption mode of adsorbing, by the adsorption part, the chemical substance during an execution time period including time period overlapping at least part of an execution time period of the first detection mode, second adsorption mode of, after the first adsorption mode, adsorbing, by the adsorption part, the chemical substance with the sample gas being caused to flow along direction from the adsorption part toward the sensor, and second detection mode of desorbing, from the adsorption part, the chemical substance adsorbed in the first and second adsorption modes and detecting the chemical substance by the sensor.

14 Claims, 6 Drawing Sheets

(56) References Cited

U.S. PATENT DOCUMENTS

| | | | |
|---|---|---|---|
| 6,345,545 B1 * | 2/2002 | Linker | G01N 1/405 73/863.23 |
| 6,914,220 B2 * | 7/2005 | Tian | H05B 3/26 219/385 |
| 7,101,661 B1 * | 9/2006 | Heller | C07H 21/00 422/68.1 |
| 8,281,642 B2 * | 10/2012 | Lee | G01N 27/127 73/23.31 |
| 8,300,218 B2 * | 10/2012 | Furtaw | G01N 21/3504 356/72 |
| 10,408,715 B2 * | 9/2019 | Murashima | G01N 30/80 |
| 11,137,368 B2 * | 10/2021 | Stowell | G01N 27/4145 |
| 11,243,198 B2 * | 2/2022 | Lin | G01N 33/0006 |
| 11,415,570 B2 * | 8/2022 | Chou | G01N 1/2813 |
| 11,543,333 B2 * | 1/2023 | Cho | G01N 1/2214 |
| 2009/0090197 A1 | 4/2009 | Finlay et al. | |
| 2009/0113991 A1 | 5/2009 | Saito et al. | |
| 2018/0038776 A1 * | 2/2018 | Murashima | G01N 30/08 |
| 2018/0149565 A1 | 5/2018 | Nakao et al. | |
| 2018/0153439 A1 * | 6/2018 | Miller | G01N 21/31 |
| 2019/0170619 A1 * | 6/2019 | Nakao | G01N 1/405 |
| 2020/0096490 A1 * | 3/2020 | Hanai | G01N 33/0011 |
| 2020/0158625 A1 * | 5/2020 | Naor | G01N 21/01 |

FOREIGN PATENT DOCUMENTS

| | | |
|---|---|---|
| JP | 2007-017427 A | 1/2007 |
| JP | 2016-090257 A | 5/2016 |
| WO | 2017/047041 A1 | 3/2017 |

* cited by examiner

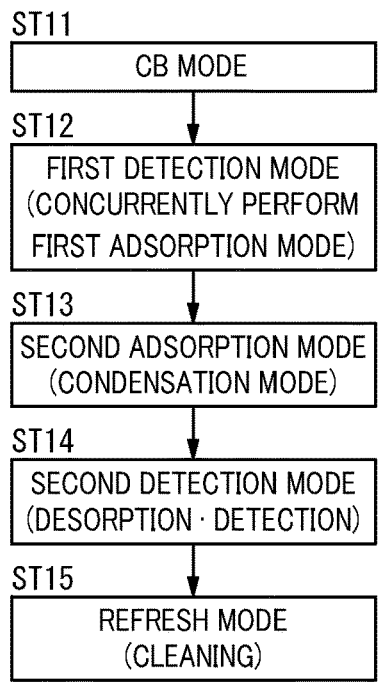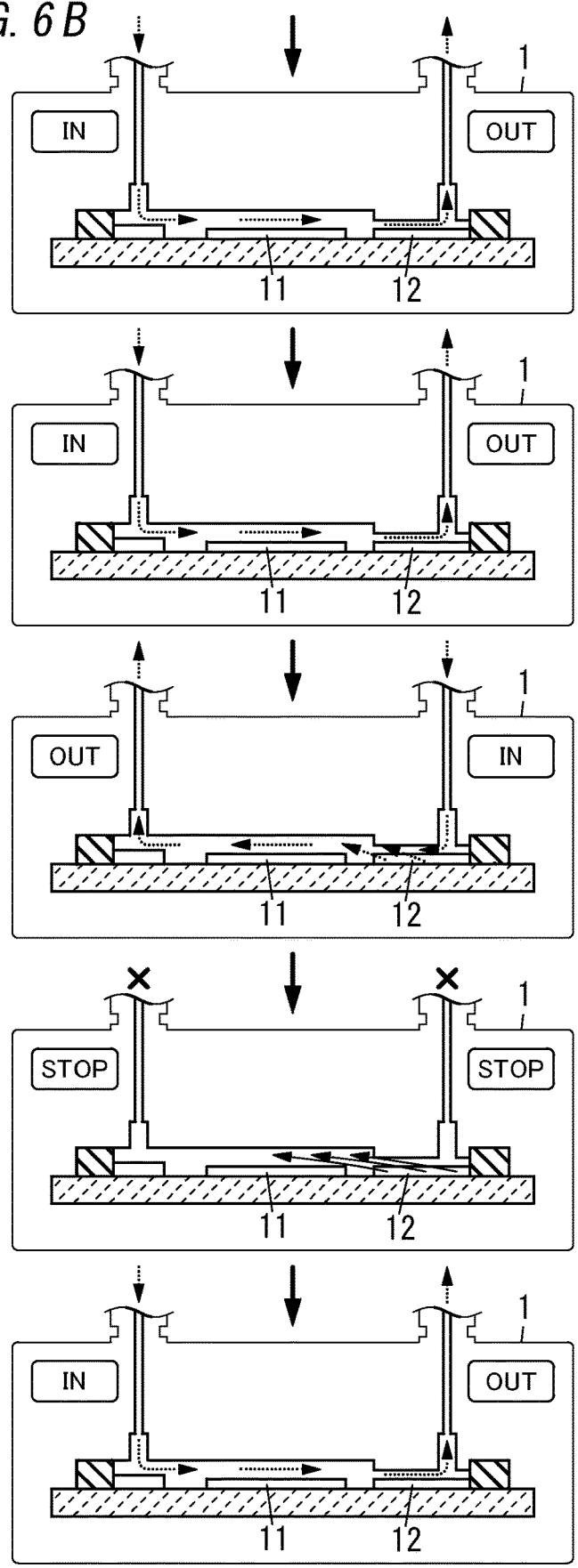
FIG. 6A
FIG. 6B

DETECTION METHOD FOR DETECTION DEVICE, CONTROL SYSTEM, DETECTION SYSTEM, AND PROGRAM

CROSS-REFERENCE OF RELATED APPLICATIONS

This application is the U.S. National Phase under 35 U.S.C. § 371 of International Patent Application No. PCT/JP2019/030916, filed on Aug. 6, 2019, which in turn claims the benefit of Japanese Application No. 2018-149789, filed on Aug. 8, 2018, the entire disclosures of which Applications are incorporated by reference herein.

TECHNICAL FIELD

The present disclosure generally relates to detection methods for detection devices, control systems, detection systems, and programs. The present disclosure specifically relates to a detection method for detection device for detecting a chemical substance existing in a gas, a control system for controlling the detection device, a detection system including the detection device, and a program.

BACKGROUND ART

As a conventional example, Patent Literature 1 describes an odor detector. The odor detector includes: an odor sensor configured to output signals corresponding to respective odor substances; an adsorption and desorption part configured to adsorb and desorb a sample gas; and a flow passage configured to guide the gas desorbed from the adsorption and desorption part to the odor sensor. In this odor detector, the adsorption and desorption part and the odor sensor are disposed independently of each other and are connected to each other via a flow path (pipe) and a switching valve.

A flow path structure of the odor detector described in Patent Literature 1 is a structure including the flow path (pipe) and the switching valve between the adsorption and desorption part and the odor sensor, and therefore, the flow path structure is complicated. Moreover, a certain time may be required for condensation of the odor substance (a chemical substance) in the sample gas toward the adsorption and desorption part, and reducing the time required for the condensation of the chemical substance is thus desirable.

CITATION LIST

Patent Literature

Patent Literature 1: JP H 10-19862 A

SUMMARY OF INVENTION

In view of the foregoing, it is an object of the present disclosure to provide a detection method for a detection device, a control system, a detection system, and a program which reduce a time required for condensation of a chemical substance while simplifying a flow path of a gas.

A detection method for a detection device according to one aspect of the present disclosure is a detection method for a detection device including a detection chamber forming part of a flow path through which a sample gas flows, an adsorption part, and a sensor. The adsorption part is disposed in the detection chamber and is configured to adsorb a chemical substance contained in the sample gas. The sensor is disposed in the detection chamber and is configured to detect the chemical substance contained in the sample gas. The detection method includes a calibration mode, a first detection mode, a first adsorption mode, a second adsorption mode, and a second detection mode. The calibration mode is a mode of calibrating the sensor in a state where a low-concentration gas is caused to flow along a direction from the sensor toward the adsorption part. A content of the chemical substance is less in the low-concentration gas than in the sample gas. The first detection mode is a mode of, after the calibration mode, detecting the chemical substance contained in the sample gas by the sensor in a state where the sample gas is caused to flow along the direction from the sensor toward the adsorption part. The first adsorption mode is a mode of adsorbing, by the adsorption part, the chemical substance during an execution time period including a time period overlapping at least part of an execution time period of the first detection mode. The second adsorption mode is a mode of, after the first adsorption mode, adsorbing, by the adsorption part, the chemical substance in a state where the sample gas is caused to flow along a direction from the adsorption part toward the sensor. The second detection mode is a mode of desorbing, from the adsorption part, the chemical substance adsorbed in the first adsorption mode and the second adsorption mode and detecting the chemical substance by the sensor.

A control system according to one aspect of the present disclosure is configured to control the detection device. The detection device includes: a detection chamber forming part of a flow path through which a sample gas flows; an adsorption part; and a sensor. The adsorption part is disposed in the detection chamber and is configured to adsorb a chemical substance contained in the sample gas. The sensor is disposed in the detection chamber and is configured to detect the chemical substance contained in the sample gas. The control system includes a calibration mode, a first detection mode, a first adsorption mode, a second adsorption mode, and a second detection mode as operation modes. The calibration mode is a mode of calibrating the sensor in a state where a low-concentration gas is caused to flow along a direction from the sensor toward the adsorption part. A content of the chemical substance is less in the low-concentration gas than in the sample gas. The first detection mode is a mode of, after the calibration mode, detecting the chemical substance contained in the sample gas by the sensor in a state where the sample gas is caused to flow along the direction from the sensor toward the adsorption part. The first adsorption mode is a mode of adsorbing, by the adsorption part, the chemical substance during an execution time period including a time period overlapping at least part of an execution time period of the first detection mode. The second adsorption mode is a mode of, after the first adsorption mode, adsorbing, by the adsorption part, the chemical substance in a state where the sample gas is caused to flow along a direction from the adsorption part toward the sensor. The second detection mode is a mode of desorbing, from the adsorption part, the chemical substance adsorbed in the first adsorption mode and the second adsorption mode and detecting the chemical substance by the sensor.

A detection system according to one aspect of the present disclosure includes the control system, the detection device, and a valve configured to open and close a pathway connected to the detection chamber. The control system is configured to perform opening and closing control of the valve to control a flow of the sample gas and the low-concentration gas in the detection chamber.

A program according to one aspect of the present disclosure is a program configured to cause a computer system to execute the detection method.

BRIEF DESCRIPTION OF DRAWINGS

FIG. 6A is a view illustrating a variation of the detection method for (the method for using) the detection device; and FIG. 6B is a view illustrating a variation of the detection method for (the method for using) the detection device.

DESCRIPTION OF EMBODIMENTS (1) Schema

The drawings to be referred to in the following description of the embodiment are all schematic representations. That is to say, the ratio of the dimensions (including thicknesses) of respective constituent elements illustrated on the drawings does not always reflect their actual dimensional ratio.

Figure 1:
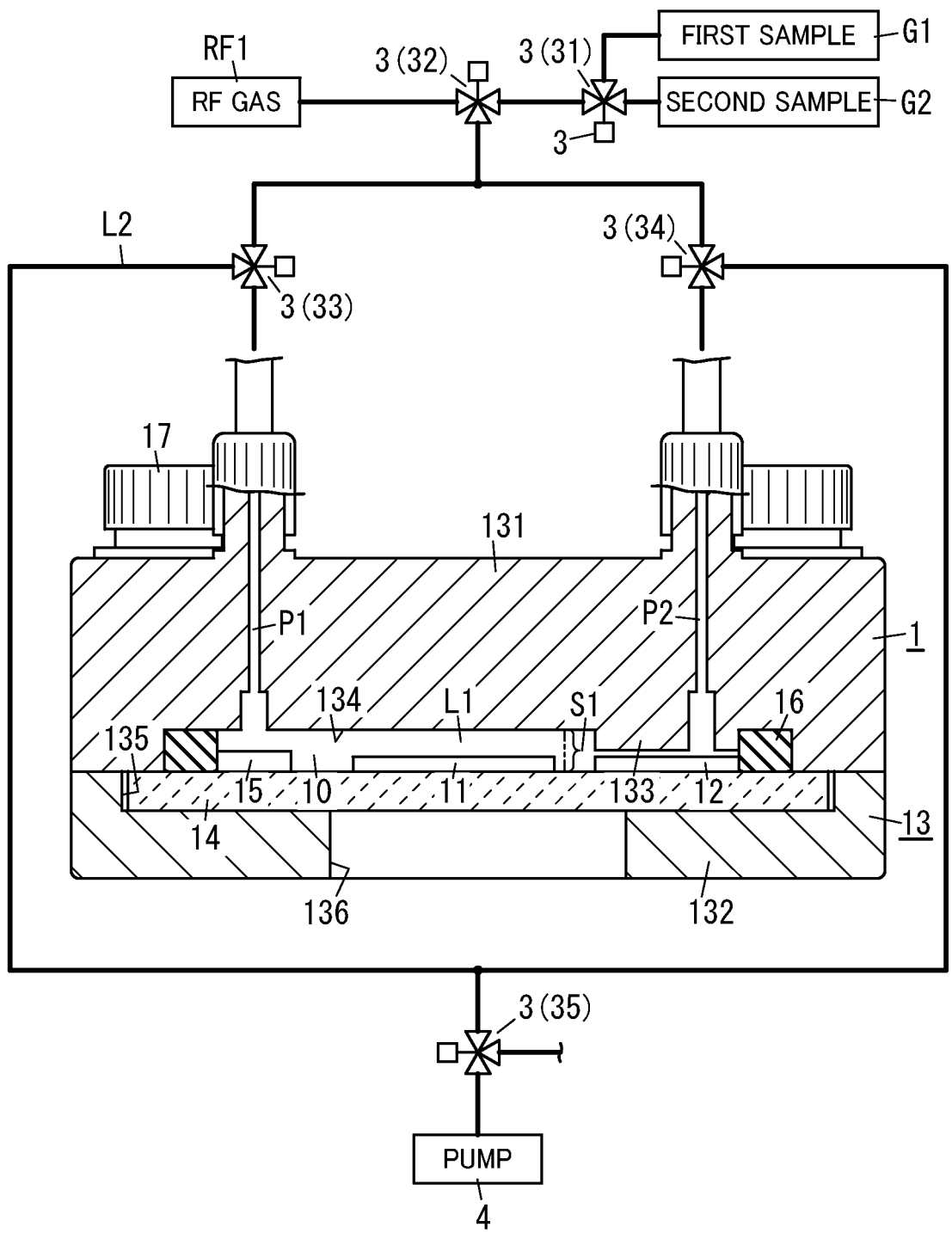
FIG. 1 is a sectional view illustrating a detection device to which a detection method (a method of use) according to an embodiment of the present disclosure is directed.

A detection method according to the present embodiment is a detection method for a detection device 1. As illustrated in FIG. 1, the detection device 1 has a detection chamber 10 forming part (a flow path L1) of a flow path of a gas (a sample gas). The detection device 1 is configured to detect a chemical substance existing in the gas in the detection chamber 10. That is, the detection device 1 further includes a sensor 11 disposed in the detection chamber 10 and configured to detect the chemical substance contained in the sample gas. The detection device 1 further includes an adsorption part 12 disposed in the detection chamber 10 and configured to adsorb the chemical substance.

The sensor 11 configured to output a signal according to the chemical substance and the adsorption part 12 configured to adsorb the chemical substance are disposed in the detection chamber 10. That is, both the sensor 11 and the adsorption part 12 are disposed in the detection chamber 10 through which the gas can passes.

In this embodiment, the detection method for (hereinafter also referred to as a method for using) the detection device 1 has at least a first detection mode, a condensation mode (hereinafter also referred to as a "second adsorption mode"), and a second detection mode. In the following description, for example, it is assumed that a control system 2 (see FIG. 2) has the first detection mode, the condensation mode, and the second detection mode as operation modes. However, at least some of these modes may be manually executed by a user (e.g., a measurer who measures the chemical substance in the gas by using the detection device 1).

The first detection mode is a mode in which the chemical substance is detected based on an output signal from the sensor 11 in a state where at least part of the gas (the sample gas) is flowing in the detection chamber 10 along a direction in the order from the sensor 11 to the adsorption part 12 (from left to right in FIG. 1). In the following description, it is assumed, for example, that the first detection mode corresponds to a calibration mode in which the sensor 11 is calibrated.

As used herein, "at least part of the gas" means a relatively large amount of overall gas flowing in the detection chamber 10. That is, the directionality of the flow of the gas (fluid) is significantly ununiform in the detection chamber 10 and may be disturbed to a certain extent, but in the first detection mode, the directionality thereof is basically the direction in the order from the sensor 11 to the adsorption part 12. That is, the first detection mode is a mode in which the chemical substance is detected by the sensor 11 in a state where (at least part of) the sample gas is caused to flow along the direction from the sensor 11 toward the adsorption part 12. In the embodiment, the control system 2 has a first adsorption mode in which the chemical substance is adsorbed by the adsorption part 12 during an execution time period including a time period overlapping at least part of an execution time period of the first detection mode. Specifically, the first detection mode and the first adsorption mode do not have to match each other in terms of an execution timing and the length of the execution time period as long as their execution time periods at least partially overlap each other. The first adsorption mode may be started before a timing at which the first detection mode is started or may be started after the timing at which the first detection mode is started. The first adsorption mode may be ended before a timing at which the first detection mode is ended or may be ended after the timing at which the first detection mode is ended. The execution time period of the first adsorption mode may be longer than or shorter than the execution time period of the first detection mode.

When the control system 2 has the calibration mode in addition to the first detection mode, the first detection mode is a mode in which after the calibration mode, the chemical substance is detected by the sensor 11 in a state where the sample gas is caused to flow in the direction from the sensor 11 toward the adsorption part 12.

The condensation mode (the second adsorption mode) is a mode in which the chemical substance is condensed by being adsorbed on the adsorption part 12. That is, the condensation mode is a mode in which molecules (the chemical substance) contained in the gas are captured by the adsorption part 12. In this embodiment, the condensation mode is executed after the first detection mode. In particular, the condensation mode is a mode in which the chemical substance is condensed by being adsorbed on the adsorption part 12 in a state where at least part of the gas is flowing in the detection chamber 10 along a direction in the order from the adsorption part 12 to the sensor 11. In other words, the condensation mode (the second adsorption mode) is a mode in which after the first adsorption mode, the chemical substance is adsorbed on the adsorption part 12 in a state where (at least part of) the sample gas is caused to flow along the direction from the adsorption part 12 toward the sensor 11.

The second detection mode detects the chemical substance based on the signal in a state where the chemical substance condensed in the condensation mode (i.e., a large number of captured molecules) is desorbed from the adsorption part 12. The "desorption" is caused by, for example, heating the adsorption part 12. In other words, the second detection mode is a mode in which the chemical substance adsorbed in the first adsorption mode and the second adsorption mode is desorbed from the adsorption part 12, and the chemical substance is detected by the sensor 11.

Here, in the present embodiment, adsorption of the chemical substance (the first adsorption mode) is performed in the first detection mode before adsorption of the chemical substance in the condensation mode (the second adsorption mode). That is, the chemical substance is adsorbed on the adsorption part 12 in a state where at least part of the gas is flowing along the direction in the order from the sensor 11 to the adsorption part 12.

Since this configuration adopts the detection device 1 in which the sensor 11 and the adsorption part 12 are disposed in the detection chamber 10 forming part (the flow path L1) of the flow path of the gas (the sample gas), the flow path L1 is simplified unlike the flow path structure in the odor detector described in Patent Literature 1. Moreover, since the adsorption of the chemical substance is performed in the first detection mode before the adsorption of the chemical substance in the condensation mode, a time required to condense the chemical substance in the condensation mode can be reduced. That is, the adsorption of the chemical substance is precedently performed in the first adsorption mode, and therefore, a time required for the adsorption of the chemical substance in the second adsorption mode can be reduced. In particular, a direction in which the gas flows in the second adsorption mode (the condensation mode) is the direction from the adsorption part 12 toward the sensor 11, and therefore, the time required for the adsorption of the chemical substance can be reduced.

(2) Details (2.1) Overall Configuration

Overall configuration of the detection system 100 including the detection device 1 according to the present embodiment will be described in detail below. The detection system 100 includes the control system 2, a plurality of (in FIG. 1, five) valves 3, and a pump 4 in addition to the above-described detection device 1.

(2.2) Detection Device

The detection device 1 is configured to detect the chemical substance in the gas in the detection chamber 10 serving as the flow path L1 of the gas (the sample gas) as described above. Examples of the "chemical substance" mentioned herein include a volatile organic compound and an inorganic compound. Examples of volatile organic compound include ketones, amines, alcohols, aromatic carbon hydrides, aldehydes, esters, organic acid, methyl mercaptan, and disulfide. Examples of the inorganic compound include hydrogen sulfide, sulfur dioxide, and carbon disulfide.

As illustrated in FIG. 1, the detection device 1 includes a housing 13, a substrate 14, a temperature and humidity sensor 15, a seal member 16, and the like in addition to the sensor 11 and the adsorption part 12 described above.

Figure 3A:
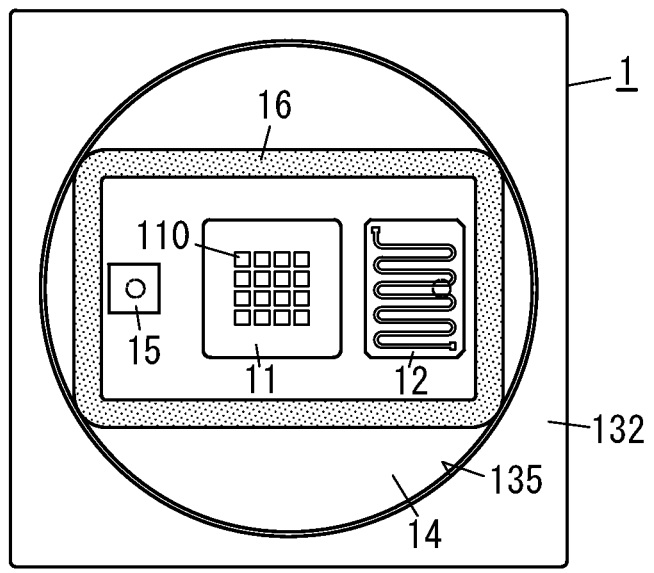
FIG. 3A is a top view illustrating the detection device where an upper cover of the housing of the detection device is removed.
Figure 3B:
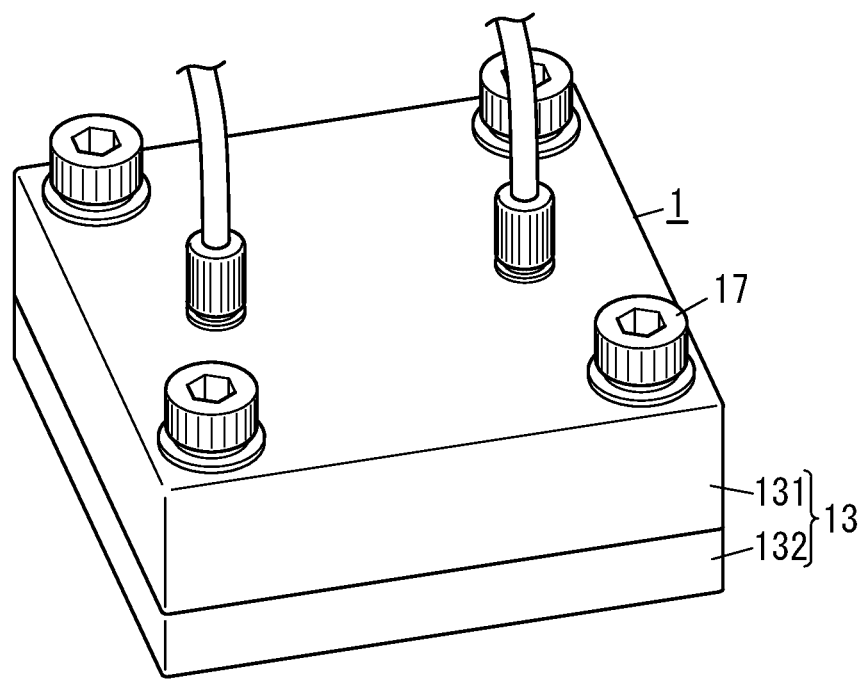
FIG. 3B is a perspective view illustrating the detection device.

The housing 13 is made of, for example, a polyether ether ketone (PEEK) resin to have a rectangular box shape. As illustrated in FIG. 3B, the housing 13 includes, for example, an upper cover 131 and a lower case 132 and has a vertically split structure. The upper cover 131 and the lower case 132 are assembled together by, for example, screwing their four corners with four hexagon socket screws 17.

The upper cover 131 has a surface which faces the lower case 132 and which has a recess 134 (see FIG. 1) recessed in a direction away from the lower case 132. The lower case 132 has a surface which faces the upper cover 131 and which has a recess 135 (see FIG. 1) recessed in a direction away from the upper cover 131. The substrate 14 is accommodated in the recess 135. The recess 135 has a bottom which has a pore 136 formed as a through hole.

The recess 134 can form, together with the substrate 14 in the recess 135, a space serving as the flow path L1 of the gas when the upper cover 131 and the lower case 132 are assembled together. The space corresponds to the detection chamber 10. Note that to suppress the gas from leaking to the outside of the housing 13 from a gap between the upper cover 131 and the lower case 132, the seal member 16 (e.g., an O-ring) is fitted along an inner peripheral surface of the recess 134. The seal member 16 is pressed against the substrate 14 in a state where the seal member 16 is in the recess 134, thereby sealing the gap.

In addition, the upper cover 131 has two flow path ports (hereinafter referred to as a first flow path port P1 and a second flow path port P2) through which the gas can flow into or out from the detection chamber 10. Each flow path port is spatially communicated with the recess 134. In this embodiment, the first flow path port P1 is a flow path port on the left in FIG. 1, and the second flow path port P2 is a flow path port on the right in FIG. 1. Each of the first flow path port P1 and the second flow path port P2 can be an inlet or an outlet of the gas in accordance with the operation mode of the control system 2 (which will be described later). The first flow path port P1 and the second flow path port P2 are connected to a pathway L2 on which the five valves 3 are disposed. Note that the pathway L2 is constituted by a plumbing tube or the like.

Moreover, as illustrated in FIG. 1, the upper cover 131 has a protruding rib 133 in the recess 134. The protruding rib 133 will be described in detail later in "(2.6) Protruding Rib".

The substrate 14 is a printed wiring board made of, for example, an epoxy resin. As illustrated in FIG. 3A, the substrate 14 has a circular shape in plan view (when viewed from above). The substrate 14 has a conductor part formed in a pattern on its surface. The temperature and humidity sensor 15, the sensor 11, and the adsorption part 12 are mounted on a mounting surface (in FIG. 1, an upper surface) of the substrate 14 to be aligned in this order from the left. In other words, the sensor 11 is disposed substantially at the center of the mounting surface of the substrate 14, and the temperature and humidity sensor 15 and the adsorption part 12 are disposed on respective sides of the sensor 11 in the rightward/leftward direction. Various electronic components in addition to the above-mentioned components may be mounted on the substrate 14.

The substrate 14 is fit in the recess 135 in the lower case 132 such that the mounting surface of the substrate 14 faces the detection chamber 10. In addition, part of a back surface (in FIG. 1, a lower surface) of the substrate 14 is exposed outside through the pore 136 at the bottom of the recess 135. The first flow path port P1 has an opening end located at a side of the recess 134 and facing the temperature and humidity sensor 15. The second flow path port P2 has an opening end located at a side of the recess 134 and facing the adsorption part 12.

The sensor 11 is a chip-type component having a rectangular shape in plan view (when viewed from above). The sensor 11 is disposed in the detection chamber 10 in a state where the sensor 11 is mounted on the mounting surface of the substrate 14. The sensor 11 has one or more sensor elements 110. In the present disclosure, for example, 16 sensor elements 110 are disposed in a 4×4 matrix as illustrated in FIG. 3A. In sum, the sensor 11 is, for example, a sensor array including a plurality of sensor elements 110.

The sensor 11 detects the chemical substance in the gas in the detection chamber 10 to output a signal (a detection signal) according to the chemical substance. The sensor elements 110 have, for example, respective detection properties different from each other. The detection signal includes a plurality of individual signals to be output from each sensor element 110.

The type of the sensor 11 is not particularly limited. As the sensor 11, for example, a semiconductor sensor, an electrochemical sensor, a surface acoustic wave element, a field effect transistor biosensor (FET biosensor), an optical sensor, or the like may be used.

The detection signal (an electric signal) of the sensor 11 is transmitted to the outside of the detection device 1 through a signal line (not shown) electrically connected from a side of the back surface of the substrate 14 via the pore 136 to the conductor part of the substrate 14.

The adsorption part 12 is a chip-type component having a rectangular shape in plan view (when viewed from above). The adsorption part 12 includes, for example, an adsorbent and a gas transmission layer.

The adsorbent has a property of adsorbing the chemical substance when coming into contact with the chemical substance and desorbing the chemical substance when being heated. The adsorbent is, for example, an aggregate of nanowires which are electrically conductive. The adsorbent is configured by, for example, bundling a plurality of nanowires such that a gap is formed between the nanowires. The chemical substance enters the gap between the nanowires and is easily adsorbed on the nanowires.

Materials for the nanowires are not limited as long as the nanowires have the property of adsorbing at least one kind of chemical substance. The nanowire contains, for example, metal oxide such as $SnO_2$, $ZnO$, $In_2O_3$, $In_{2-x}Sn_xO_3$ (e.g., $0.1 \leq x \leq 0.2$), $NiO$, $CuO$, $TiO_2$, $SiO_2$; metal such as Al, Ag, Au, Pd, Pt; carbon; or silicon. When the nanowire contains the carbon, the nanowire is, for example, a carbon nanotube.

The nanowire may include: a core in the shape of a wire; and a shell which is a membrane covering the core. In this case, the shell preferably has the property of adsorbing at least one kind of chemical substance. The core may contain the metal oxide, metal, carbon, or silicon as described above, or may contain a resin. The shell contains, for example, the metal oxide as described above.

The adsorption property of the adsorption part 12 depends on the material for the adsorbent, specifically, the material for the overall nanowires or the material for the shell. That is, the kind of the chemical substance to be adsorbed on the adsorption part 12 can be changed by changing the material for the overall nanowires or the material for the shell.

The gas transmission layer of the adsorption part 12 covers at least part of the adsorbent. The gas transmission layer is configured to reduce the influence of moisture over the adsorption property of a portion which is part of the adsorbent and which is covered with the gas transmission layer. Materials for the gas transmission layer are not particularly limited as long as they have a gas transmission property. The gas transmission layer contains, for example, a resin which has a gas transmission property.

Moreover, the adsorption part 12 includes a first electrode, a second electrode, and a conductive layer. The first electrode and the second electrode are electrically connected to the adsorbent via the conductive layer. When these electrode causes a current to flow through the adsorbent having a conductive property, the adsorbent generates Joule heat. The adsorbent may cause self-heating due to the Joule heat. The heat generated by the adsorbent allows the chemical substance adsorbed on the adsorption part 12 to be desorbed from the adsorbent. In sum, the adsorbent of the adsorption part 12 has both a function of adsorbing the chemical substance and a function of desorbing the chemical substance by heat.

The current to the adsorbent of the adsorption part 12 is supplied by a feeder 22 under control by a controller 21 of the control system 2. The feeder 22 is electrically connected to the conductor part of the substrate 14 by a feed line via the pore 136 at the side of the back surface of the substrate 14.

The temperature and humidity sensor 15 is a chip-type component having a rectangular shape in plan view (when viewed from above). The temperature and humidity sensor 15 is disposed in the detection chamber 10 in a state where the temperature and humidity sensor 15 is mounted on the mounting surface of the substrate 14. The temperature and humidity sensor 15 detects the temperature and the humidity of the gas in the detection chamber 10 and outputs a signal (an electric signal) according to the temperature and the humidity. The electric signal from the temperature and humidity sensor 15 is transmitted to the outside of the detection device 1 through a signal line (not shown) electrically connected from the side of the back surface of the substrate 14 via the pore 136 to the conductor part of the substrate 14.

The controller 21 of the control system 2 may acquire information regarding the temperature and the humidity based on the electric signal from the temperature and humidity sensor 15 and may perform control regarding the heat generation in, for example, the adsorption part 12. That is, the controller 21 may monitor the information regarding the temperature and the humidity to perform feedback control of the volume of a current supplied from the feeder 22.

(2.3) Pathway of Gas and Valves

Here, the pathway L2, the plurality of (five) valves 3, and the pump 4 to which the detection device 1 is connected will be described with reference to FIGS. 4A and 4B. In the detection system 100 of the present disclosure, for example, a reference gas RF1, a first sample (gas) G1, and a second sample (gas) G2 are connected to the pathway L2 in advance. Then, these gases are selectively allowed to flow into the detection chamber 10 of the detection device 1 by opening and closing control of the valves 3. That is, the valve 3 opens and closes the pathway L2 communicated with the detection chamber 10.

Figure 4A:
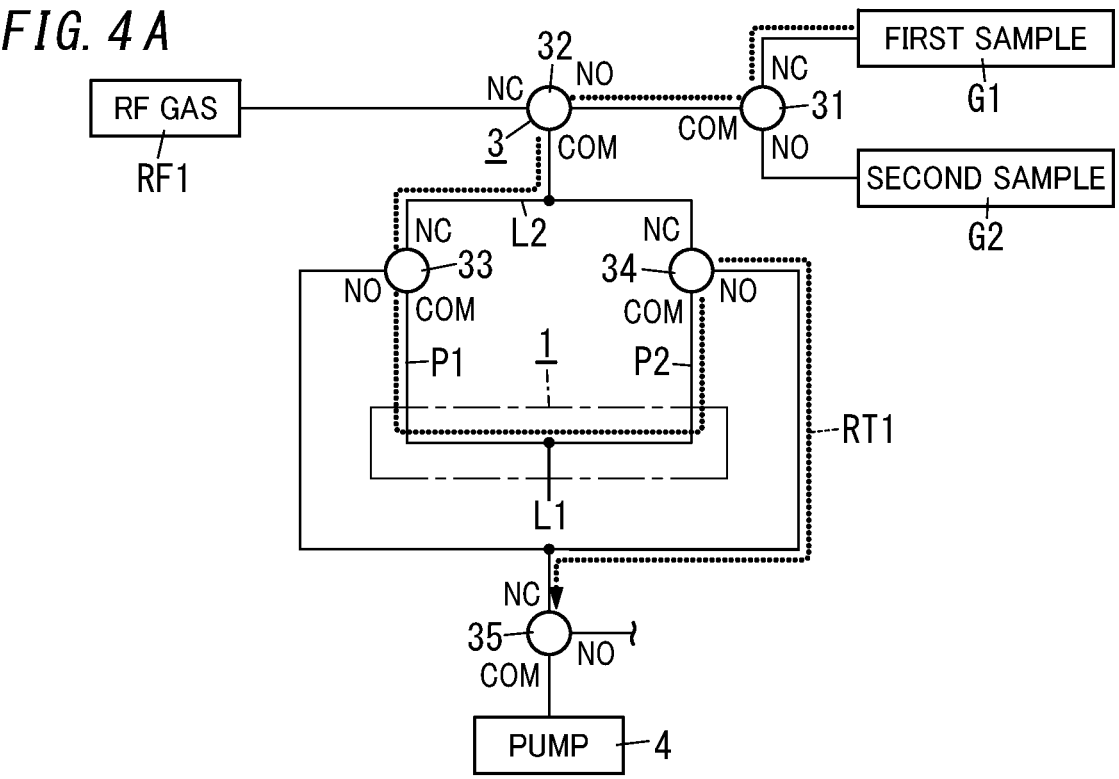
FIG. 4A is a view illustrating a pathway of a gas in the detection system.
Figure 4B:
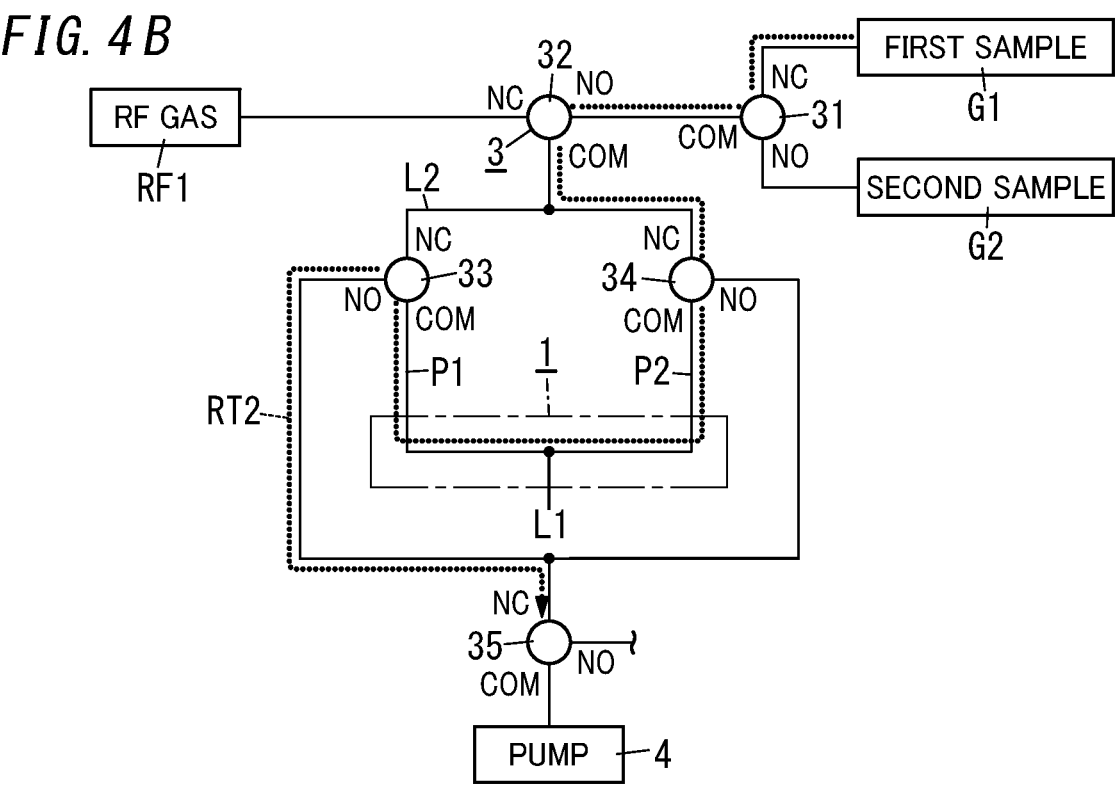
FIG. 4B is a view illustrating a pathway of a gas in the detection system.

Note that in FIGS. 1, 4A, and 4B, the first sample G1 and the second sample G2 are illustrated, but none of FIGS. 1, 4A, and 4B intends to mean that these gases have a mutual relationship, and the first sample G1 and the second sample G2 are illustrated to describe that switching of different kinds of gases is easily performed by opening or closing the valve. The first sample G1 and the second sample G2 are assumed to be, but are not limited to, gases having components similar to components of, for example, atmosphere. The first sample G1 may be air (surrounding gas) in a prescribed space, for example, on a road or in a building. The second sample G2 may be, for example, aspirated air of a living body such as a human.

In the following description, the valve 3 located closest to the first sample G1 and the second sample G2 may be referred to as a first valve 31, and the valve 3 located between the first valve 31 and the reference gas RF1 may be referred to as a second valve 32. Moreover, from the second valve 32, the pathway L2 is branched into two ways, the valve 3 disposed at a side of the first flow path port P1 of the detection device 1 may be referred to as a third valve 33, and the valve 3 disposed at a side of the second flow path port P2 of the detection device 1 may be referred to as a fourth valve 34. The valve 3 located closest to the pump 4 may be referred to as a fifth valve 35.

The valves 3 have, for example, the same configuration and are three-way electromagnetic valves (three-way solenoid valves) configured to switch the flow path directions of the gas. These valves 3 are disposed in the pathway L2 to switch the flow path directions of the gas in the pathway L2. Each valve 3 has a normally closed port (hereinafter referred to as an NC port), a normally open port (hereinafter referred to as an NO port), and a common port (hereinafter referred to as a COM port).

For example, regarding the first valve 31, the NC port is connected to the first sample G1, the NO port is connected to the second sample G2, and the COM port is connected to the second valve 32. Regarding the second valve 32, the NC port is connected to the reference gas RF1, the NO port is connected to the first valve 31, and the COM port is connected to the third valve 33 and the fourth valve 34.

Regarding the third valve 33, the NC port is connected to the second valve 32, the NO port is connected to the fifth valve 35, the COM port is connected to the first flow path port P1 of the detection device 1. Regarding the fourth valve 34, the NC port is connected to the second valve 32, the NO port is connected to the fifth valve 35, the COM port is connected to the second flow path port P2 of the detection device 1. Regarding the fifth valve 35, the NC port is connected to the third valve 33 and the fourth valve 34, the NO port is in an unused state, and the COM port is connected to the pump 4.

In the present disclosure, each valve 3 is electrically connected to the control system 2, and the control system 2 performs switching control of opening and closing of the NC port and the NO port of each valve 3. Note that each valve 3 is, as described above, a solenoid valve but is not particularly limited, and one or more of the plurality of valves 3 may be electrically operated valves or manual valves. In the case of the manual valve, a measurer of the chemical substance may manually perform switching operation of opening and closing at an appropriate timing.

Moreover, the structure of the pathway L2 shown in FIGS. 4A and 4B is a mere example, and the number, the arrangement, and the like of the valves 3 are not particularly limited. Moreover, the kind and the number of kinds of the reference gas and the sample gas are not particularly limited. For example, a measurer of the chemical substance may manually change connection of the first sample (gas) G1 or the second sample (gas) G2 selectively to the NO port of the second valve 32. In this case, the first valve 31 may be omitted.

The pump 4 in the present disclosure is a suction pump. The pump 4 operates to suck the gas in the detection chamber 10. In other words, the pump 4 applies a negative pressure to the detection chamber 10. Thus, an airflow is produced in the flow path L1. Note that the pump 4 is not limited to the suction pump. The pump 4 may be a pressurizing pump, and in this case, the pump 4 is disposed upstream in the pathway L2, and the pathway L2 may be configured to send the gas to the detection chamber 10. Moreover, a pump does not have to be used, and, for example, a blast fan may be used instead of the pump as long as it produces an airflow in the flow path L1.

(2.4) Control System

The control system 2 is configured to perform opening and closing control of the five valves 3 to control the flow of the gas in the detection chamber 10 of the detection device 1. The control system 2 is configured to perform operation control of the detection device 1 (the sensor 11, the adsorption part 12, the temperature and humidity sensor 15, and the like) and the pump 4. The control system 2 has an analyzing function of analyzing the chemical substance when receiving the detection signal of the sensor 11. Note that the control system 2 may issue an instruction of analysis by transmitting information based on the detection signal of the sensor 11 to an analyzer separately provided.

Figure 2:
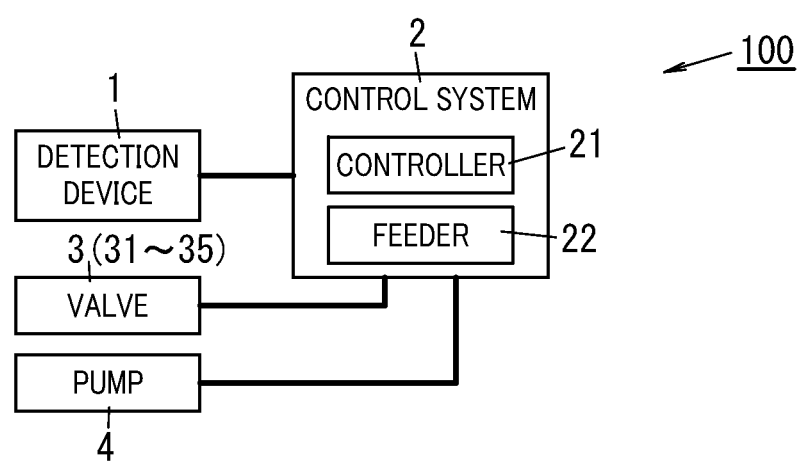
FIG. 2 is a block diagram illustrating a detection system according to the embodiment of the present disclosure.

As illustrated in FIG. 2, the control system 2 includes the controller 21 and the feeder 22. The functions of the controller 21 and the feeder 22 in the control system 2 may all be implemented by a single device accommodated in one housing or may be implemented by a plurality of distributed devices.

The controller 21 may be implemented as, for example, a microcontroller including, as major constituent elements, a Central Processing Unit (CPU) and a memory. That is to say, the controller 21 is implemented as a computer including a CPU and a memory. The computer performs the function of the controller 21 by making the CPU execute a program stored in the memory. In this embodiment, the program is stored in the memory in advance. However, the program may be provided over a telecommunications network such as the Internet, or as a recording medium such as a memory card storing the program therein.

The controller 21 sends a drive signal to each valve 3 which is a solenoid valve, thereby opening and closing each valve 3. When the valve 3 is switched on by receiving the drive signal, the NC port enters an open state, and the NO port in turn enters a closed state. Moreover, when the valve 3 is switched off, the NC port returns to the closed state, and the NO port returns to the open state.

The feeder 22 includes a power supply circuit and the like, and the controller 21 controls the feeder 22 to supply operation power to the detection device 1. In particular, the controller 21 controls the feeder 22 as described above to cause a current to flow through the adsorbent of the adsorption part 12, thereby heating the adsorbent to desorb the chemical substance.

Incidentally, the control system 2 of the present disclosure includes the first detection mode, the first adsorption mode, the condensation mode (the second adsorption mode), the second detection mode, and a refresh mode as operation modes. Specifically, the controller 21 performs opening and closing control of the five valves 3 and operation control of the pump 4 in each mode, thereby controlling the airflow of the gas in the detection chamber 10 of the detection device 1.

The first detection mode corresponds to the calibration mode (hereinafter referred to as a CB mode) in which calibration of the sensor 11 is performed. An error may occur in the detection signal (a measured value) of the sensor 11 due to, for example, aging degradation or a production error of the sensor 11. Thus, calibration is required to specify the ability of the sensor 11 alone by the control system 2. In particular, when the concentration of the chemical substance in the sample gas is satisfactorily low, the calibration can be performed with the sample gas being deemed to be a gas containing no chemical substance. That is, zero point correction of the sensor 11 is performed based on the measured value in the first detection mode. Performing the calibration provides a calibration curve (e.g., the relationship between the concentration and the intensity) relating to the sample gas in the sensor 11 alone. A gas used in the CB mode may be a pure gas containing no chemical substance which is a measurement target (e.g., a nitrogen gas) as described later in variations or the reference gas RF1 which may contain only a small amount of chemical substance, and in this embodiment, the first sample G1 is used. The first sample G1 is used as a gas for the calibration based on the perspective that a very low concentration of the chemical substance in the first sample G1 is expected already before measurement. In sum, in this embodiment, the first sample G1 containing the chemical substance which is the measurement target is used also in the first detection mode (the CB mode) and is further used in the second detection mode.

The controller 21 performs, in the first detection mode, the calibration (determination of a correction value) based on the detection signal of the sensor 11 in a state where the first sample G1 is caused to flow in the detection chamber 10. Here, the calibration is performed in a state where (at least part of) the gas is flowing in the detection chamber 10 along the direction in the order from the sensor 11 to the adsorption part 12. Specifically, the controller 21 controls opening and closing of the valves 3 and operation of the pump 4 such that the first sample G1 flows along a first route RT1 in FIG. 4A toward the pump 4. Moreover, the controller 21 executes the first adsorption mode in which the chemical substance is adsorbed by the adsorption part 12 during an execution time period including a time period overlapping at least part of an execution time period of the first detection mode.

The condensation mode (the second adsorption mode) is a mode in which the chemical substance is condensed by being adsorbed on the adsorption part 12. That is, the condensation mode is a mode in which molecules (the chemical substance) contained in the gas are captured by the adsorption part 12. In this embodiment, the condensation mode is executed after the first detection mode and the first adsorption mode.

The controller 21 causes the first sample G1 to flow in the detection chamber 10 in the condensation mode. However, the direction in which the gas flows is different from that in the first detection mode. That is, condensation is performed in a state where (at least part of) the gas is flowing in the detection chamber 10 along the direction in the order from the adsorption part 12 to the sensor 11. Specifically, the controller 21 controls opening and closing of the valves 3 and operation of the pump 4 such that the first sample G1 flows along a second route RT2 in FIG. 4B toward the pump 4.

The second detection mode detects (measures) the chemical substance based on the detection signal of the sensor 11 in a state where the chemical substance condensed in the condensation mode (i.e., a large number of captured molecules) is desorbed.

The controller 21 stops the first sample G1 to flow into the detection chamber 10 in the second detection mode. Specifically, the controller 21 switches off, for example, the third valve 33, the fourth valve 34, and the fifth valve 35, that is, changes the state of the NC ports of these valves to the closed state. Moreover, the controller 21 stops the pump 4. Thus, the detection chamber 10 becomes a substantially hermetically closed space. Moreover, the controller 21 heats the adsorption part 12 by current supply from the feeder 22 in the second detection mode and causes the chemical substance captured by the adsorption part 12 to be desorbed. As a result, the concentration of the chemical substance in the first sample G1 in the detection chamber 10 can be increased.

The refresh mode is a mode in which after measurement of the first sample G1 ends, that is, after the second detection mode, the gas is caused to flow along the direction in the order from the sensor 11 to the adsorption part 12 to refresh (clean) the adsorption part 12. The controller 21 causes the reference gas RF1 to flow into the detection chamber 10 in the refresh mode. In the refresh mode, a direction into which the gas flows downstream of the second valve 32 is substantially common to the direction in the first detection mode (see the first route RT1 in FIG. 4A). However, the gas used is different from that in the first detection mode and is the reference gas RF1.

Moreover, the controller 21 heats the adsorption part 12 by the current supply from the feeder 22 also in the refresh mode. That is, while the adsorption part 12 is heated, the reference gas RF1 is caused to flow in the above-described direction. As a result, while the chemical substance is suppressed from being attached to the sensor 11, the adsorption part 12 can be refreshed.

Note that when the concentration of the chemical substance in the first sample G1 is relatively low, the gas used may be the first sample G1 also in the refresh mode.

(2.5) Method for using Detection Device

The method for using the detection device 1 will be described below with reference to FIGS. 5A and 5B. An example in which the first sample G1 is adopted as the measurement target will be described below.

Figure 5A:
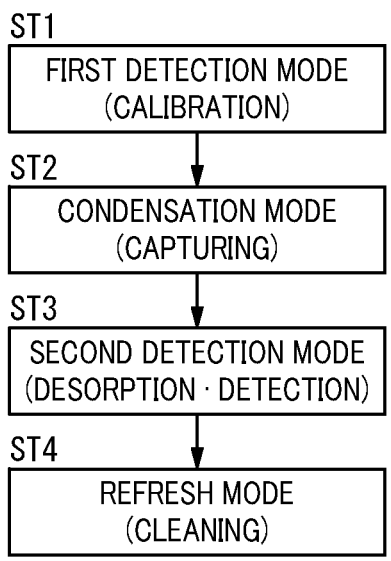
FIG. 5A is a view illustrating the detection method for (the method for using) the detection device.

The method for using the detection device 1 has the first detection mode (the CB mode) (FIG. 5A: step ST1). First of all, the first sample G1 is caused to flow along the first route RT1 in the first detection mode. That is, the first valve 31, the third valve 33, and the fifth valve 35 are switched on, and in addition, the pump 4 is operated. The second valve 32 and the fourth valve 34 are switched off. As a result, the first sample G1 flows along the direction in the order from the sensor 11 to the adsorption part 12 as shown in the uppermost schematic diagram in FIG. 5B. In this state, the sensor 11 is calibrated. Moreover, in the first detection mode, the adsorption part 12 also adsorbs the chemical substance in the first sample G1. In other words, the first adsorption mode in which the chemical substance is adsorbed by the adsorption part 12 is executed during an execution time period including a time period overlapping at least part of an execution time period of the first detection mode. Note that a time required for the first detection mode is, for example, about 120 seconds.

Moreover, the method for using the detection device 1 has the condensation (capturing) mode (FIG. 5A: step ST2). In the condensation mode, the first sample G1 is caused to flow along the second route RT2. That is, the first valve 31, the fourth valve 34, and the fifth valve 35 are switched on, and in addition, the pump 4 is operated. The second valve 32 and the third valve 33 are switched off. As a result, the first sample G1 flows along the direction in the order from the adsorption part 12 to the sensor 11 as illustrated in the second uppermost schematic diagram in FIG. 5B. In this state, the chemical substance in the first sample G1 is condensed by being adsorbed on the adsorption part 12. Note that a time required for the condensation mode is, for example, about 180 seconds.

Moreover, the method for using the detection device 1 has the second detection mode (FIG. 5A: step ST3). In the second detection mode, the airflow of the first sample G1 is stopped. That is, the third valve 33, the fourth valve 34, and the fifth valve 35 are switched off, and the pump 4 is stopped. As a result, the detection chamber 10 is in a state substantially sealed as illustrated in the third uppermost schematic diagram in FIG. 5B. Then, in a state where the chemical substance condensed in the condensation mode is desorbed (by being heated), the chemical substance is detected based on the detection signal of the sensor 11. That is, in the second detection mode, the chemical substance adsorbed in the first adsorption mode and the second adsorption mode is desorbed from the adsorption part 12, and the chemical substance is detected by the sensor 11. Note that a time required for the second detection mode is, for example, about 10 seconds. Moreover, a target temperature of the heating is, for example, 200° C.

Moreover, the method for using the detection device 1 has the refresh (cleaning) mode (FIG. 5A: step ST4). In the refresh mode, the reference gas RF1 is caused to flow along the first route RT1. That is, the second valve 32, the third valve 33, and the fifth valve 35 are switched on, and in addition, the pump 4 is operated. The first valve 31 and the fourth valve 34 are switched off. As a result, the reference gas RF1 flows along the direction in the order from the sensor 11 to the adsorption part 12 as shown in the lowermost schematic diagram in FIG. 5B. Note that a time required for the refresh mode is, for example, about 10 seconds.

As described above, in the method for using the present disclosure, the chemical substance is adsorbed in the first detection mode before adsorption of the chemical substance in the condensation mode. Thus, the time required to condense the chemical substance can be reduced. That is, the adsorption of the chemical substance is precedently performed in the first adsorption mode, and therefore, a time required for the adsorption of the chemical substance in the second adsorption mode can be reduced. In particular, the condensation mode requires the longest time as compared to the other modes. Thus, adsorption of the chemical substance is performed also in a preparation stage which is the CB mode, which can effectively reduce an overall measurement time.

Moreover, since the detection device 1 in which the sensor 11 and the adsorption part 12 are disposed in the same detection chamber 10 is used, the flow path L1 is simplified unlike the flow path structure in the odor detector described in Patent Literature 1.

Moreover, in the second detection mode, the detection result (a correction value result of the calibration) in the first detection mode is used to detect the chemical substance, and therefore, a detection result with increased reliability can be obtained. In particular, in the first detection mode, detection is performed in a state where the gas is flowing along the direction in the order from the sensor 11 to the adsorption part 12, and thus, the first detection mode is suitable for the calibration. That is, as compared to a case where the gas flows in a direction in which the gas passes the adsorption part 12 before the sensor 11, the flow of the gas passing on the sensor 11 can be made more uniform.

Meanwhile, condensation is performed in the condensation mode in a state where the gas is flowing along the direction in the order from the adsorption part 12 to the sensor 11 in contrary to the first detection mode, and therefore, the condensation (adsorption) to the adsorption part 12 can be more effectively performed. This is because if condensation were performed in a state where the gas is flowing along the direction in the order from the sensor 11 to the adsorption part 12, quite a few amount of chemical substances would be attach to the sensor 11 before the chemical substances reach the adsorption part 12. Thus, the time required to condense the chemical substance can be further reduced.

(2.6) Protruding Rib

Incidentally, the housing 13 of the present embodiment has a structure in which the flow path L1 has a cross-sectional area S1 (see FIG. 1) which is orthogonal to the direction from the adsorption part 12 toward the sensor 11 and which increases from the adsorption part 12 toward the sensor 11. In this embodiment, the structure is formed by, for example, the protruding rib 133 (see FIG. 1). In other words, the detection device 1 has the protruding rib 133.

The protruding rib 133 protrudes toward the adsorption part 12 from a region which is in a bottom surface of the recess 134 of the upper cover 131 and which faces the adsorption part 12. The protruding rib 133 is a rectangular flat base when viewed from the adsorption part 12 (from below). The surface area of the protruding rib 133 is not particularly limited but is desirably slightly larger than the surface area of the adsorption part 12. A gap having a prescribed dimension is provided between the protruding rib 133 and the adsorption part 12 in the vertical direction. Note that the protruding rib 133 is disposed on an inner side of the seal member 16. Moreover, the opening of the second flow path port P2 is provided at the protruding rib 133.

For example, the height of the protruding rib 133 is 0.75 mm, the thickness of the adsorption part 12 is 0.5 mm, and the prescribed dimension is 0.25 mm. That is, the dimension between the upper surface and the lower surface in the detection chamber 10 is, for example, 1.5 mm. Note that these numerical values are mere examples and should not be construed as limiting.

Figure 5B:
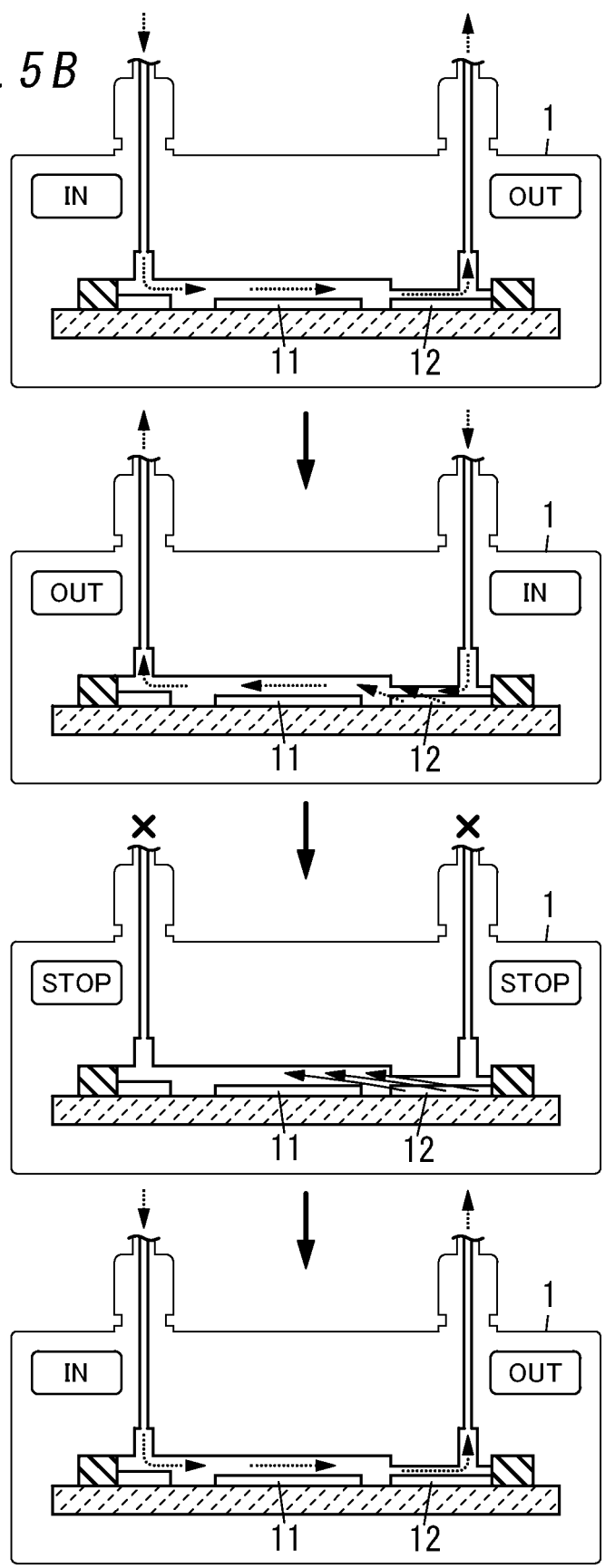
FIG. 5B is a view illustrating the detection method for (the method for using) the detection device.

Providing the protruding rib 133 increases the possibility that a turbulent flow of the gas is caused in the gap, which is relatively narrow, when the gas flows from the second flow path port P2 toward the adsorption part 12 as illustrated in the second uppermost diagram in FIG. 5B in the condensation mode. That is, a time in which part of the gas resides in the gap increases, and the adsorption of the chemical substance is thus further promoted. Thus, the time required to condense the chemical substance can be further reduced.

Note that in the example shown in the figure, the protruding rib 133 reduces the height (upward and downward direction) of part of the flow path L1, thereby achieving the structure in which the cross-sectional area S1 increases from the adsorption part 12 toward the sensor 11. Alternatively, the width (in the depth direction in FIG. 1) of part of the flow path L1 may be narrowed to achieve the structure in which the cross-sectional area S1 increases from the adsorption part 12 toward the sensor 11.

(3) Variation

The above-described embodiment is a mere example of various embodiments of the present disclosure. Various modifications may be made to the above-described embodiment depending on design and the like as long as the object of the present disclosure is achieved. Moreover, functions similar to those of the detection device 1 and the control system 2 according to the above-described embodiment may be implemented by a control method of the detection device 1 and the control system 2, a computer program, or a non-transitory recording medium or the like in which a computer program is stored.

Variations of the above-described embodiment will be described below. Note that any of the variations to be described below may be combined as appropriate. In the following description, the above-described embodiment will be sometimes referred to as a "basic example".

The controller 21 of the control system 2 of the present disclosure includes a computer system. The computer system includes, as principal hardware components, a processor and a memory. The processor executes a program stored in the memory of the computer system, thereby implementing functions as the controller 21 of the control system 2 in the present disclosure. The program may be stored in the memory of the computer system in advance, provided via a telecommunications network, or provided as a non-transitory recording medium such as a computer system-readable memory card, optical disc, or hard disk drive storing the program. The processor of the computer system may be made up of a single or a plurality of electronic circuits including a semiconductor integrated circuit (IC) or a large-scale integrated circuit (LSI). The integrated circuit such as IC or LSI mentioned herein may be referred to in another way, depending on the degree of the integration and includes integrated circuits called system LSI, very-large-scale integration (VLSI), or ultra-large-scale integration (ULSI). A Field-Programmable Gate Array (FPGA), which is programmable after fabrication of the LSI, or a logical device which allows reconfiguration of connections in LSI or reconfiguration of circuit cells in LSI may be adopted as the processor. Those electronic circuits may be either integrated together on a single chip or distributed on multiple chips, whichever is appropriate. The plurality of chips may be collected in one device or may be distributed in a plurality of devices. As mentioned herein, the computer system includes a microcontroller including one or more processors and one or more memories. Thus, the microcontroller is also composed of one or more electronic circuits including a semiconductor integrated circuit or a large-scale integrated circuit.

Moreover, collecting a plurality of functions of each of the detection device 1 and the control system 2 in a single housing is not an essential configuration for each of the detection device 1 and the control system 2, and these components may be distributed in a plurality of housings. Moreover, at least some functions of each of the detection device 1 and the control system 2, for example, some functions of the control system 2, may be implemented by cloud (cloud computing) or the like. Conversely, a plurality of functions of the control system 2 may be collected in a single housing as in the basic example.

(3.1) Variation Related to Calibration

In the basic example, it is assumed that the first detection mode corresponds to the CB mode. However, the CB mode may be provided separately from the first detection mode. The present variation will be described below with reference to FIGS. 6A and 6B.

In the present variation, a detection method for (a method for using) a detection device 1 further has a CB mode in addition to a first detection mode, a first adsorption mode, a condensation mode (a second adsorption mode), a second detection mode, and a refresh mode. However, the refresh mode is not an essential mode in the present disclosure, and the detection method for the detection device 1 does not have to have the refresh mode.

In the present variation, the CB mode (FIG. 6A: step ST11) is set before the first detection mode (FIG. 6A: step ST12). Specifically, a control system 2 performs the CB mode, the first detection mode (the first adsorption mode is concurrently executed in, for example, an execution time period of the first detection mode), the condensation mode (the second adsorption mode), the second detection mode, and the refresh mode in this order as operation modes. Note that when detection (measurement) of a chemical substance is repeatedly executed, the refresh mode performed for the first time may correspond to a CB mode performed for the second time, and hereafter, a refresh mode performed for the second time may correspond to a CB mode performed for the third time. That is, the refresh mode may also serve as the CB mode.

Now, for example, if a relatively high concentration of the chemical substance in a first sample G1 is expected already before the measurement, causing the first sample G1 to flow in the CB mode as in the case of the basic example may be inappropriate in some cases. In consideration of this point, a reference gas RF1 is used in the CB mode in the present variation. That is, the reference gas RF1 corresponds to a low-concentration gas whose content of the chemical substance is less than that of the sample gas.

The first detection mode in the present variation corresponds to a simple detection mode with respect to the second detection mode corresponding to "full detection" after the condensation mode. That is, the control system 2 detects (measures) the chemical substance based on a detection signal of a sensor 11 by causing the first sample G1 (or a second sample G2) to flow in the first detection mode, as in the second detection mode. However, the first detection mode is different from the second detection mode in that desorption is not performed in the first detection mode. Moreover, as the "simple" detection, for example, a threshold lower than a threshold for concentration determination used in analysis of a measurement result in the second detection mode may be used. Note that to the route of the gas in the first detection mode in the present variation, a first route RT1 is applied in a similar manner to the basic example. Thus, as compared to a case where a second route RT2 is applied, that is, as compared to a case where the gas flows in a direction in which the gas passes an adsorption part 12 before the sensor 11, it is possible to reduce the possibility that the chemical substance is captured by the adsorption part 12 before the chemical substance is detected by the sensor 11.

In the basic example, the time required for the first detection mode is, for example, 120 seconds because the first detection mode corresponds to the CB mode. However, in the present variation, the first detection mode may be, for example, about 10 seconds similarly to the second detection mode.

In the present variation, a controller 21 of the control system 2 is configured to determine, based on a detection result in the first detection mode, whether or not the transition of the operation mode to the condensation mode (the second adsorption mode) and the second detection mode has to be made. In other words, the controller 21 has a function of determining whether or not it is necessary to proceed to the full detection. For example, when measured data (e.g., concentration data of the chemical substance) obtained in the first detection mode exceeds a specified threshold, the controller 21 determines that it is not necessary to proceed to the full detection.

The control system 2 desirably includes a presentation unit (e.g., a display) to present its determination result to a user (e.g., a measurer). For example, when the controller 21 determines that it is not necessary to proceed to the full detection, the controller 21 may present its determination result to the measure by using the presentation unit, and in addition, the controller 21 may stop or maintain the operation mode without causing the operation mode to transition to the condensation mode.

In sum, if the concentration of the chemical substance in the first sample G1 is relatively high, necessary and satisfactory measured data may possibly be obtained from results in the CB mode and the first detection mode without performing the detection in the condensation mode. As in the present variation, when the control system 2 has the above-described functions, it is also possible that the operation mode does not transition to the condensation mode and to the second detection mode depending on the result in the first detection mode. As a result, a time taken by the condensation mode and the second detection mode may be omitted. Moreover, if it is determined that it is necessary to proceed to the full detection, a time required for the condensation of the chemical substance can be reduced in a similar manner to the basic example since adsorption of the chemical substance is performed in advance in the first detection mode.

As can be seen from the above description, the CB mode (step ST11), the first detection mode (step ST12), the second adsorption mode (step ST13), the second detection mode (step ST14), and the refresh mode (step ST15) are executed in this order (see FIG. 6A).

In the CB mode, the sensor 11 is calibrated in a state where the reference gas RF1 (the low-concentration gas) is caused to flow along the direction from the sensor 11 toward the adsorption part 12 as illustrated in the uppermost schematic diagram in FIG. 6B.

In the first detection mode, the chemical substance is detected by the sensor 11 in a state where the sample gas (the first sample G1 or the second sample G2) is caused to flow along the direction from the sensor 11 toward the adsorption part 12 as illustrated in the second uppermost schematic diagram in FIG. 6B. In the first adsorption mode, for example, the adsorption part 12 concurrently adsorbs the chemical substance in the execution time period of the first detection mode.

In the second adsorption mode, the adsorption part 12 adsorbs the chemical substance in a state where the sample gas (the first sample G1 or the second sample G2) is caused to flow along the direction from the adsorption part 12 toward the sensor 11 as illustrated in the third uppermost schematic diagram in FIG. 6B.

In the second detection mode, the chemical substance adsorbed in the first adsorption mode and the second adsorption mode is desorbed from the adsorption part 12 as illustrated in the fourth uppermost schematic diagram in FIG. 6B, and the chemical substance is detected by the sensor 11.

In the refresh mode, the adsorption part 12 is refreshed (cleaned) with the reference gas RF1 (the low-concentration gas) being caused to flow along the direction from the sensor 11 toward the adsorption part 12 as illustrated in the lowermost schematic diagram in FIG. 6B.

Note that as an alternative to that the controller 21 has the function of determining whether or not it is necessary to proceed to the full detection, a user (e.g., a measurer) himself/herself may determine whether or not it is necessary to proceed to the full detection based on the measured data obtained in the CB mode and the first detection mode.

Moreover, each of the CB mode and the first detection mode may be executed a prescribed number of times (two or more times). For example, the CB mode and the first detection mode are alternately performed, and after each of the CB mode and the first detection mode are executed a prescribed number of times, whether or not it is necessary to proceed to the full detection may be determined.

(3.2) Other Variations

In the basic example, the number of each of the sensor 11 and the adsorption part 12 is one. However, the number of these components are not particularly limited. For example, a plurality of sensors 11 may be provided. Moreover, the positional relationship between the sensor 11 and the adsorption part 12 is not limited to such an arrangement that the sensor 11 and the adsorption part 12 are aligned in a line on the substrate 14. That is, the number and the arrangement of the sensor 11 and the adsorption part 12 are not particularly limited as long as a state where (at least part of) the gas is flowing in the detection chamber 10 along the direction in the order from the sensor 11 to the adsorption part 12 can be achieved in the first detection mode. Specifically, for example, one adsorption part 12 may be disposed substantially at the center on the mounting surface of the substrate 14, and two or more sensors 11 may be arranged on the mounting surface of the substrate 14 to surround the adsorption part 12.

Moreover, the number of the flow path ports is two (the first flow path port P1 and the second flow path port P2) in the basic example but is not limited to two. For example, three or more flow path ports may be provided, and in addition, their apertures may be different from each other.

In the basic example, the detection chamber 10 is a closed space during the second detection mode. However, in the second detection mode, the flow rate of the gas in the detection chamber 10 is at least lower than in the first detection mode, and the detection chamber 10 does not have to be a closed space. Reducing the flow rate of the gas in the second detection mode to be lower than the flow rate (e.g., 50 ml/min to 500 ml/min) of the gas in the first detection mode can efficiently increase the concentration of the chemical substance in the flow path L1. However, as in the basic example, when the flow rate of the gas in the second detection mode is set to substantially zero, that is, when the detection chamber 10 is a substantially hermetically closed space, the possibility that the sensor 11 detects the chemical substance increases, and the concentration of the chemical substance can be further efficiently increased.

In the basic example, the pump 4 is stopped to stop the airflow of the gas in the second detection mode such that the detection chamber 10 is in the closed state. However, in the second detection mode, for example, the pump 4 or another suction means is operated to achieve a state where the pressure is lower than at least the atmospheric pressure (desirably a nearly vacuum state) in the detection chamber 10, and then, heating may be performed to desorb the chemical substance. In this case, it is possible to increase the possibility that desorbed molecules (the chemical substance) uniformly moves toward the sensor 11.

For example, when the first sample G1 is surrounding gas, the reference gas RF1 may be a gas obtained by causing the first sample G1 to flow through a filter, or the reference gas RF1 may be a commercially available pure gas.

In the control system 2 of the basic example, a control program for causing the operation modes to be executed may be rewritable in accordance with the detection device 1. That is, functions of the above-described operation modes in accordance with the kinds of the sensor 11 and the adsorption part 12 may be provided by updating the control program of the control system 2. A rewriting control program may be provided over a telecommunications network such as the Internet or may be provided as a recording medium such as a memory card storing the rewriting control program therein.

At least some functions of the control system 2 may be provided in the detection device 1. For example, a function relating to the calibration or the analysis of the chemical substance may be in the detection device 1.

In the basic example, the refresh mode is performed after the second detection mode. However, the refresh mode may be performed before the first detection mode. In the case of the variation in "(3.1)" above, the refresh mode may be performed before the CB mode. Moreover, the refresh mode may be accordingly omitted or may be performed only when the surrounding gas of the measurement target changes or only once in a prescribed time period (e.g., once per day).

In the basic example, energizing the adsorbent having a conductive property achieves heating of the adsorption part 12. However, as a heating means for the adsorption part 12, a heater may be separately provided.

(4) Advantages

As described above, a detection method for (a method for using) a detection device (1) according to a first aspect is a detection method for the detection device (1) including: a detection chamber (10) forming part (a flow path L1) of a flow path through which a sample gas flows; an adsorption part (12); and a sensor (11). The adsorption part (12) is disposed in the detection chamber (10) and is configured to adsorb a chemical substance contained in the sample gas. The sensor (11) is disposed in the detection chamber (10) and is configured to detect the chemical substance contained in the sample gas. The detection method includes a calibration mode, a first detection mode, a first adsorption mode, a second adsorption mode, and a second detection mode. The calibration mode is a mode of calibrating the sensor (11) in a state where a low-concentration gas is caused to flow along a direction from the sensor (11) toward the adsorption part (12). A content of the chemical substance is less in the low-concentration gas than in the sample gas. The first detection mode is a mode of, after the calibration mode, detecting the chemical substance contained in the sample gas by the sensor (11) in a state where the sample gas is caused to flow along the direction from the sensor (11) toward the adsorption part (12). The first adsorption mode is a mode of adsorbing, by the adsorption part (12), the chemical substance during an execution time period including a time period overlapping at least part of an execution time period of the first detection mode. The second adsorption mode is a mode of, after the first adsorption mode, adsorbing, by the adsorption part (12), the chemical substance in a state where the sample gas is caused to flow along a direction from the adsorption part (12) toward the sensor (11). The second detection mode is a mode of desorbing, from the adsorption part (12), the chemical substance adsorbed in the first adsorption mode and the second adsorption mode and detecting the chemical substance by the sensor (11). According to the first aspect, the detection device (1) is used in which the sensor (11) and the adsorption part (12) are disposed in the detection chamber (10) forming part (the flow path L1) of the flow path of the sample gas. Therefore, the flow path (L1) is simplified unlike the flow path structure in the odor detector described in Patent Literature 1. Moreover, the adsorption (the first adsorption mode) of the chemical substance is performed in the first detection mode before the adsorption of the chemical substance in the second adsorption mode (the condensation mode), and therefore, a time required in the condensation mode to condense the chemical substance is reduced. In particular, a direction in which a gas flows in the second adsorption mode (the condensation mode) is the direction from the adsorption part (12) toward the sensor (11), and therefore, a time required for the adsorption of the chemical substance is reduced. Moreover, since the calibration mode is executed, a detection result with further increased reliability is obtained.

In a detection method for the detection device (1) of a second aspect referring to the first aspect, whether or not to proceed to the second adsorption mode and to the second detection mode is preferably determined based on a detection result in the first detection mode. According to the second aspect, for example, when necessary and satisfactory measured data of the chemical substance is obtained from the detection result in the first detection mode, a detection result in the second detection mode no longer have to be obtained. In other words, since the operation mode may not proceed to the second adsorption mode (the condensation mode) and the second detection mode depending on the detection result in the first detection mode, a time taken by the second adsorption mode (the condensation mode) and the second detection mode may be omitted.

In a detection method for the detection device (1) of a third aspect referring to the first or second aspect, the detection chamber (10) has a cross-sectional area (S1) which is orthogonal to the direction from the adsorption part (12) toward the sensor (11) and which preferably increases from the adsorption part (12) toward the sensor (11). The third aspect increases, for example, the possibility that a turbulent flow of the gas is caused in the second adsorption mode (the condensation mode) and further promotes condensation (adsorption) of the chemical substance on the adsorption part (12). Thus, the time required to condense the chemical substance can be further reduced.

In a detection method for the detection device (1) of a fourth aspect referring to any one of the first to third aspects, a flow rate of the gas in the detection chamber (10) is preferably lower in the second detection mode than in the first detection mode. According to the fourth aspect, the concentration of the chemical substance in the flow path (L1) is efficiently increased.

A detection method for the detection device (1) of a fifth aspect referring to any one of the first to fourth aspects preferably further has a refresh mode after the second detection mode. In the refresh mode, the gas is caused to flow in the direction from the sensor (11) toward the adsorption part (12). According to the fifth aspect, the adsorption part (12) is refreshed (cleaned) while the chemical substance is suppressed from being attached to the sensor (11).

A control system (2) of a sixth aspect is configured to control the detection device (1). The detection device (1) includes: a detection chamber (10) forming part (a flow path L1) of a flow path through which a sample gas flows; an adsorption part (12); and a sensor (11). The adsorption part (12) is disposed in the detection chamber (10) and is configured to adsorb a chemical substance contained in the sample gas. The sensor (11) is disposed in the detection chamber (10) and is configured to detect the chemical substance contained in the sample gas. The control system (2) includes a calibration mode, a first detection mode, a first adsorption mode, a second adsorption mode, and a second detection mode as operation modes. The calibration mode is a mode of calibrating the sensor (11) in a state where a low-concentration gas is caused to flow along a direction from the sensor (11) toward the adsorption part (12). A content of the chemical substance is less in the low-concentration gas than in the sample gas. The first detection mode is a mode of, after the calibration mode, detecting the chemical substance contained in the sample gas by the sensor (11) in a state where the sample gas is caused to flow along the direction from the sensor (11) toward the adsorption part (12). The first adsorption mode is a mode of adsorbing, by the adsorption part (12), the chemical substance during an execution time period including a time period overlapping at least part of an execution time period of the first detection mode. The second adsorption mode is a mode of, after the first adsorption mode, adsorbing, by the adsorption part (12), the chemical substance in a state where the sample gas is caused to flow along a direction from the adsorption part (12) toward the sensor (11). The second detection mode is a mode of desorbing, from the adsorption part (12), the chemical substance adsorbed in the first adsorption mode and the second adsorption mode and detecting the chemical substance by the sensor (11). The sixth aspect provides the control system (2) which is configured to reduce a time required for condensation of the chemical substance while the flow path of the gas is simplified.

In the control system (2) of a seventh aspect referring the sixth aspect, a control program for causing the operation modes to be executed is preferably rewritable in accordance with the detection device (1). According to the seventh aspect, rewriting provides a function of the control system (2) in accordance with the detection device (1).

A detection system (100) of an eighth aspect includes: the control system (2) of the sixth aspect or the seventh aspect; the detection device (1); and a valve (3) configured to open and close a pathway (L2) connected to the detection chamber (10). The control system (2) is configured to perform opening and closing control of the valve (3) to control a flow of the gas in the detection camber (10). The eighth aspect provides the detection system (100) which is configured to reduce a time required for condensation of the chemical substance while the flow path of the gas is simplified.

A program according to a ninth aspect is a program configured to cause a computer system to execute the detection method for the detection device (1) of any one of the first to fifth aspects. The ninth aspect provides a function of reducing a time required for condensation of the chemical substance while the flow path of the gas is simplified. Optionally, a non-transitory computer-readable medium may store the program. In that case, when the program is executed by a computer system, the computer system may carry out the detection method for the detection device (1) of any one of the first to the fifth aspects.

The components of the second to fifth aspects are not essential components for the detection method for the detection device (1) and may thus accordingly be omitted.

REFERENCE SIGNS LIST

100 DETECTION SYSTEM
1 DETECTION DEVICE
10 DETECTION CHAMBER
11 SENSOR
12 ADSORPTION PART
2 CONTROL SYSTEM
3 VALVE
RF1 REFERENCE GAS
S1 CROSS-SECTIONAL AREA

The invention claimed is:

1. A detection method for a detection device including a detection chamber forming part of a flow path through which a sample gas flows, an adsorption part disposed in the detection chamber and configured to adsorb a chemical substance contained in the sample gas, and a sensor disposed in the detection chamber and configured to detect the chemical substance contained in the sample gas, the detection method comprising:
a calibration mode of calibrating the sensor in a state where a low-concentration gas is caused to flow along a direction from the sensor toward the adsorption part, a content of the chemical substance being less in the low-concentration gas than in the sample gas;
a first detection mode of, after the calibration mode, detecting the chemical substance contained in the sample gas by the sensor in a state where the sample gas is caused to flow along the direction from the sensor toward the adsorption part;
a first adsorption mode of adsorbing, by the adsorption part, the chemical substance during an execution time period including a time period overlapping at least part of an execution time period of the first detection mode;
a second adsorption mode of, after the first adsorption mode, adsorbing, by the adsorption part, the chemical substance in a state where the sample gas is caused to flow along a direction from the adsorption part toward the sensor; and
a second detection mode of desorbing, from the adsorption part, the chemical substance adsorbed in the first adsorption mode and the second adsorption mode and detecting the chemical substance by the sensor.

2. The detection method of claim 1, wherein
a flow rate of the gas in the detection chamber is lower in the second detection mode than in the first detection mode.

3. The detection method of claim 1, further comprising a refresh mode after the second detection mode, wherein
in the refresh mode, the gas is caused to flow in the direction from the sensor toward the adsorption part.

4. The detection method of claim 1, wherein
the detection chamber has a cross-sectional area which is orthogonal to the direction from the adsorption part toward the sensor and which increases from the adsorption part toward the sensor.

5. The detection method of claim 4, wherein
a flow rate of the gas in the detection chamber is lower in the second detection mode than in the first detection mode.

6. The detection method of claim 1, wherein
whether or not to proceed to the second adsorption mode and to the second detection mode is determined based on a detection result in the first detection mode.

7. The detection method of claim 6, wherein
a flow rate of the gas in the detection chamber is lower in the second detection mode than in the first detection mode.

8. The detection method of claim 6, wherein
the detection chamber has a cross-sectional area which is orthogonal to the direction from the adsorption part toward the sensor and which increases from the adsorption part toward the sensor.

9. The detection method of claim 8, wherein
a flow rate of the gas in the detection chamber is lower in the second detection mode than in the first detection mode.

10. A computer-readable, non-transitory, and tangible recoding medium recording a program a computer system, the program causing computer system to execute the detection method for the detection device of claim 1.

11. A control system configured to control a detection device including a detection chamber forming part of a flow path through which a sample gas flows, an adsorption part disposed in the detection chamber and configured to adsorb a chemical substance contained in the sample gas, and a sensor disposed in the detection chamber and configured to detect the chemical substance contained in the sample gas, the control system having: as operation modes, a calibration mode of calibrating the sensor in a state where a low-concentration gas is caused to flow along a direction from the sensor toward the adsorption part, a content of the chemical substance being less in the low-concentration gas than in the sample gas;

a first detection mode of, after the calibration mode, detecting the chemical substance contained in the sample gas by the sensor in a state where the sample gas is caused to flow along the direction from the sensor toward the adsorption part;

a first adsorption mode of adsorbing, by the adsorption part, the chemical substance during an execution time period including a time period overlapping at least part of an execution time period of the first detection mode;

a second adsorption mode of, after the first adsorption mode, adsorbing, by the adsorption part, the chemical substance in a state where the sample gas is caused to flow along a direction from the adsorption part toward the sensor; and a second detection mode of desorbing from the adsorption part, the chemical substance adsorbed in the first adsorption mode and the second adsorption mode and detecting the chemical substance by the sensor.

12. A detection system, comprising:
the control system of claim 11;
the detection device; and
a valve configured to open and close a pathway connected to the detection chamber,
the control system being configured to perform opening and closing control of the valve to control a flow of the sample gas and a flow of the low-concentration gas in the detection chamber.

13. The control system of claim 11, wherein
a control program for causing the operation modes to be executed is rewritable in accordance with the detection device.

14. A detection system, comprising:
the control system of claim 13;
the detection device; and
a valve configured to open and close a pathway connected to the detection chamber,
the control system being configured to perform opening and closing control of the valve to control a flow of the sample gas and a flow of the low-concentration gas in the detection chamber.

* * * * *